Figure 1:
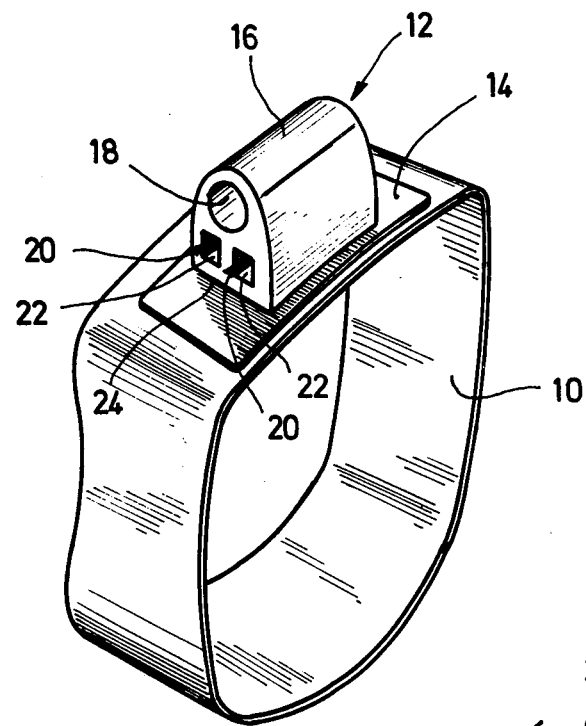

United States Patent [19]

Kraus

[11] 4,184,254
[45] Jan. 22, 1980

[54] PROCESS OF ELECTRO-ERODING CHANNELS IN MULTIPLE BUCCAL TUBE DEVICE

[75] Inventor: Hans J. Kraus, Waldbronn, Fed. Rep. of Germany

[73] Assignee: Dentaurum Hans-Peter Winkelstroeter KG, Ispringen, Fed. Rep. of Germany

[21] Appl. No.: 785,557

[22] Filed: Apr. 7, 1977

[30] Foreign Application Priority Data

Apr. 15, 1976 [DE] Fed. Rep. of Germany ....... 2616767

[51] Int. Cl.² ............................ B23P 1/00; B23P 1/04; A61C 7/00
[52] U.S. Cl. .................................... 433/17; 204/129.6; 204/224 M; 204/129.55
[58] Field of Search ..................... 204/129.35, 129.55, 204/129.6, 224 M; 32/14 A

[56] References Cited

U.S. PATENT DOCUMENTS

| | | | |
|---|---|---|---|
| 2,902,584 | 9/1959 | Ullmann | 204/224 X |
| 3,218,714 | 11/1965 | Wallshein | 32/14 A |
| 3,281,343 | 10/1966 | O'Connor | 204/129.35 X |
| 3,816,272 | 6/1974 | Joslin | 204/129.35 X |
| 3,916,526 | 11/1975 | Schudy | 32/14 A |
| 4,104,503 | 8/1978 | Di Piazza et al. | 204/129.55 X |

*Primary Examiner*—John H. Mack
*Assistant Examiner*—D. R. Valentine
*Attorney, Agent, or Firm*—Kenway & Jenney

[57] ABSTRACT

A buccal tube device has a body attached to a tooth band. The body contains at least one channel with a non-circular cross-section. The channel is formed in the body by an electroerosion process. In a preferred form, the channel cross-section is four cornered and is inclined. The invention also includes a process for forming such buccal tubes by providing an electroerosion electrode with a non-circular cross-section and using it to form a channel of corresponding cross-section. The electroerosion process may include flushing the channel thus formed during the electroerosion.

5 Claims, 2 Drawing Figures

PROCESS OF ELECTRO-ERODING CHANNELS IN MULTIPLE BUCCAL TUBE DEVICE

The invention relates to a multiple Buccal tube device having an integral body with a base for attachment to an annular tooth band, several channels, at least one of which is of non-circular cross-section, being formed in said body.

Buccal tube devices in the most varied designs are known, however, they are all rather expensive to manufacture and/or the way in which they can be used is subject to certain limitations. In a first known embodiment an inverted approximately U-shaped housing made of sheet metal comprises two flanges enabling the housing to be attached, for example, welded to a tooth band. Three seemless drawn tubes, one being of circular cross-section and the other two of square cross-section are disposed in this housing and the space between the tubes and the housing is filled with solder in order to keep the tubes in position. Obviously this method of manufacture does not enable exact positioning of the tubes in the housing. Moreover, practice has shown that the solder often flows into places where it is unwanted and does not fill out the space surrounded by the housing entirely, so that cavities are formed in which food particles can settle. Furthermore, in numerous cases where four-edged tubes are utilized it would be expedient if they were inclined relative to the attachment flanges, preferably such that the edge of the square cross-section facing the surface of the attachment flange forms with said surface an angle of 5°, 10°, 15°, 20° or 25° depending on the embodiment of the multiple Buccal tube. Obviously, precisely correct angular positioning of the four-edged tubes is not possible using the manufacturing technique described above.

The same applies to another known device where the tubes are directly soldered to the tooth band. Embodiments of this device having inclined four-edged tubes are available on the market, however, their positioning is not as exact as is desired. Furthermore, the tubes of these devices are not attached securely enough to the tooth band, which results in individual tubes repeatedly becoming detached from the accompanying tooth band during use.

Multiple Buccal tube devices comprising channels made from one single piece of sheet metal which has been bent to the correct shape and then welded to an attachment flange are also known. However, they too do not permit the desired inclined positioning to be achieved.

A multiple Buccal tube device of the type described at the beginning having a cast body comprising a channel of circular cross-section located within the body and a groove-shaped channel of right-angled cross-section located at its edge is also known. The groove-shaped channel is closed by mounting the cast body on an attachment flange. Thus, the provision of inclined four-edged channels is also impossible in this embodiment.

The object of the invention was to produce multiple Buccal tube devices comprising precisely inclined channels of non-circular cross-section. Departing from a multiple Buccal tube device of the type defined at the beginning this object is realized by the invention by the channel of non-circular cross-section being located within the body and its inner walls having the structure of a surface formed by electroerosion (ECM). Accordingly, a multiple Buccal tube device of the aforementioned kind is produced by forming the channel of non-circular cross-section by an ECM process using an electrode of corresponding cross-section. This process involves no difficulties in positioning an electrode at a precise incline relative to the fixed workpiece and then forming the desired inclined channel. The actual body of the multiple Buccal tube can be attached, especially welded, to a small plate prior or subsequent to the forming of the channels and the multiple Buccal tube device can be attached to a tooth band subsequently by means of said small plate. It is, however, also conceivable to have the body directly attached to the tooth band.

The invention is not only suited for producing multiple Buccal tubes where the cross-section of one or several channels is at an incline relative to the base, this method also makes it possible to form channels whose longitudinal axis extends at an incline to the base, should such multiple Buccal tubes be required in practical application.

Apart from the fact that the object is realized by the invention, it also has the advantage that inventive multiple Buccal tubes can be designed much more daintily than the known construction comprising a sheet metal housing with tubes inserted therein and spaces filled with solder, and furthermore, the inventive multiple Buccal tube has no cavities where food particles can settle.

Theoretically, the channels of non-circular cross-section could be formed directly by an electrode in a body which has not been previously bored. However, the channels can be formed much more quickly if a bore is first made in the longitudinal direction of the body in the area where the channel is to be formed and said bore is then flushed during the electroerosion.

A preferred embodiment of an inventive multiple Buccal tube device and how it is produced is described in the following, reference being had to the enclosed drawings.

Figure 2:
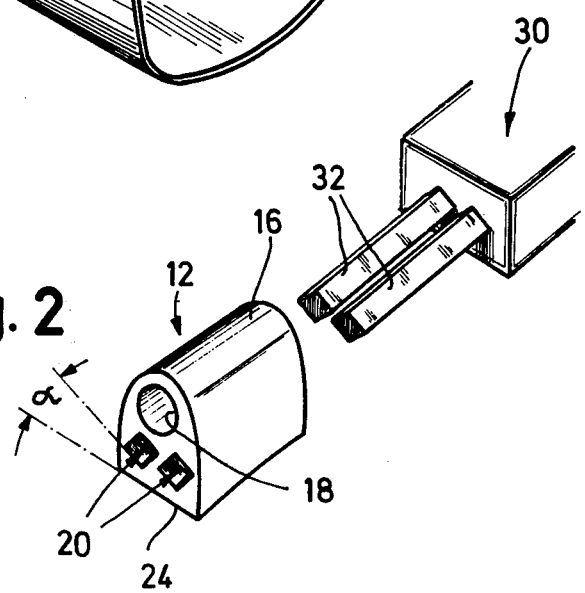

FIG. 1 is a perspective view of an annular tooth band with a multiple Buccal tube device attached to it, and FIG. 2 shows the body of this multiple Buccal tube and the electrodes of an ECM machine for forming the four-cornered channels.

FIG. 1 shows an annular tooth band 10 to which a multiple Buccal tube device designated in its entirety as 12 is attached, more particularly spot welded. The multiple Buccal tube device consists of a flange plate 14 and a body 16 attached thereto, said body comprising a bore 18 of circular cross-section and two channels 20 of square cross-section. In the embodiment shown in FIG. 1 the inner walls 22 of the channels extend parallel to the flange plate 14 and thus to the base 24 of the body 16 which is preferably made of stainless steel.

The method of producing the inventive multiple Buccal tubes will now be described, reference being had to FIG. 2. An electrode head 30 of an ECM machine comprising two electrodes 32 which can be turned about their longitudinal axis and then held in the set position are illustrated. The cross-section of the electrodes 32 corresponds to the cross-section of the channels 20 to be formed.

The bore 18 is made in the body 16 in the conventional manner, namely by means of mechanical drilling. Two bores extending approximately in the center of the channels 20 to be formed later are made in the body 16 and the channels 20 are then formed by removing material from the body 16 using the electrodes 32.

The previously made bores are simultaneously flushed, which accelerates the electroerosion process substantially.

Adjustment of the electrodes 32 by turning them about their longitudinal axis makes it possible to freely select the angle α indicated in FIG. 2 at which the channels 20 are inclined relative to the base 24 of the body 16 and maintain it exactly.

The structure of the inner walls of the channels 20 is typical of the ECM process and the material used for the production of the body 16.

I claim:

1. A multiple buccal tube device having an integral body with a base for attachment to annular tooth band and several channels formed in said body, the improvement comprising at least one of said channels having a non-circular cross-section with several corners, said non-circular channel being formed by an electroerosion process using an electrode of corresponding cross-section and wherein the inner walls of said non-circular cross-sectional channel bounded by said corners and facing said base extend at an incline with respect to said base.

2. A process for producing a multiple buccal tube device according to claim 1 comprising
providing an electroerosion electrode having a non-circular cross-section, and
forming at least one channel in said body by electroerosion using said electrode, said channel having a non-circular cross-section corresponding to that of said electrode.

3. The method as claimed in claim 2 wherein said channel forming includes producing a longitudinal bore in said body and flushing said bore during said electroerosion.

4. A mutiple buccal tube device produced by the method of claim 3.

5. A multiple buccal tube device produced by the method of claim 2.

* * * * *